US009243625B2

(12) United States Patent
Brandl et al.

(10) Patent No.: US 9,243,625 B2
(45) Date of Patent: Jan. 26, 2016

(54) PERISTALTIC PUMP HAVING ELECTRICALLY GROUNDED COMPONENTS

(75) Inventors: Matthias Brandl, Bad Koenigshofen (DE); Martin Prinz, Hammelburg (DE); Franz Pleiner, Estenfeld (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 586 days.

(21) Appl. No.: 13/505,616

(22) PCT Filed: Nov. 4, 2010

(86) PCT No.: PCT/EP2010/066777
§ 371 (c)(1),
(2), (4) Date: Jul. 24, 2012

(87) PCT Pub. No.: WO2011/054890
PCT Pub. Date: May 12, 2011

(65) Prior Publication Data
US 2012/0282126 A1  Nov. 8, 2012

(30) Foreign Application Priority Data
Nov. 4, 2009  (DE) .......................... 10 2009 046 406

(51) Int. Cl.
*F04B 43/12* (2006.01)
*F04B 43/08* (2006.01)
*A61M 1/16* (2006.01)
*A61M 1/10* (2006.01)

(52) U.S. Cl.
CPC .......... *F04B 43/1261* (2013.01); *A61M 1/1037* (2013.01); *A61M 1/1039* (2014.02); *A61M 1/16* (2013.01); *F04B 43/082* (2013.01); *F04B 43/123* (2013.01)

(58) Field of Classification Search
CPC .. F04B 43/082; F04B 43/123; F04B 43/1253; F04B 43/1261; F04B 43/1269; F04B 43/1284
USPC ................ 417/474, 476, 477.1, 477.2, 477.9, 417/477.3
See application file for complete search history.

(56) References Cited

U.S. PATENT DOCUMENTS 3,580,983 A   5/1971  Jackson
4,277,226 A * 7/1981  Archibald ....................... 417/38
(Continued)

FOREIGN PATENT DOCUMENTS

CN      1950604      4/2007
CN    101534880      9/2009
(Continued)

*Primary Examiner* — Bryan Lettman
*Assistant Examiner* — Timothy P Solak
(74) *Attorney, Agent, or Firm* — Jacobson Holman, PLLC

(57) ABSTRACT

A peristaltic pump for use in medical technology with a stator and a rotor. The stator 40 has an occlusion bed 12 which forms the contact area with a tube accommodated within, and the rotor is provided with rolling elements suitable for occluding a tube accommodated between the occlusion bed and the rolling elements. At least a part of the occlusion bed has an electrically conductive surface for reducing and/or preventing electrostatic charging of the tube. The stator may be injection molded from an electrically non-conductive plastic and the electrically conductive surface may be formed by a molded-in metallic insert or a molded-in metallic foil insert.

11 Claims, 2 Drawing Sheets

(56) References Cited

U.S. PATENT DOCUMENTS

| | | | | |
|---|---|---|---|---|
| 4,373,525 A | * | 2/1983 | Kobayashi | 417/63 |
| 5,127,907 A | * | 7/1992 | Coutre et al. | 604/151 |
| 5,324,180 A | * | 6/1994 | Zanger | 417/475 |
| RE38,869 E | * | 11/2005 | Polaschegg et al. | 604/6.09 |
| 7,001,153 B2 | | 2/2006 | McDowell et al. | |
| 8,180,443 B1 | | 5/2012 | Kleinekofort et al. | |
| 2004/0228735 A1 | * | 11/2004 | Byrne | 417/53 |
| 2005/0010077 A1 | | 1/2005 | Calderon | |
| 2005/0025647 A1 | * | 2/2005 | Ortega et al. | 417/477.1 |
| 2008/0213113 A1 | | 9/2008 | Lawrence et al. | |
| 2011/0150668 A1 | | 6/2011 | Baumann et al. | |

FOREIGN PATENT DOCUMENTS

| | | | | |
|---|---|---|---|---|
| DE | 36 633 | | 2/1965 | |
| JP | 3-65877 | * | 6/1991 | F04C 5/00 |
| JP | H03-65877 | | 6/1991 | |
| JP | 2009-243307 | | 10/2009 | |
| WO | WO 2004/108206 | | 12/2004 | |
| WO | WO 2009/044220 | | 4/2009 | |

* cited by examiner

PERISTALTIC PUMP HAVING ELECTRICALLY GROUNDED COMPONENTS

This is a national stage of PCT/EP10/066777 filed Nov. 4, 2010 and published in German, which claims the priority of German number 10 2009 046 406.9 filed Nov. 4, 2009, hereby incorporated by reference.

BACKGROUND OF THE INVENTION

1. Field of the Invention

The invention relates to a peristaltic pump for use in medical technology comprising a stator and a rotor, whereby the stator has an occlusion bed which forms the contact area with a tube accommodated within, and the rotor is provided with rolling elements suitable for occluding a tube accommodated between the occlusion bed and the rolling elements.

2. Description of the Related Art

Peristaltic pumps are used in the medical field to convey extracorporeal fluids, or to deliver them in accurate quantities. One use of peristaltic pumps is in dialysis devices, whereby dialysate in the dialysate cycle, dialysis fluid and/or blood needs to be pumped. In a peristaltic pump, a flexible tube is laid along a cylindrical inner diameter, and locally closed or occluded by pressure rollers exerting force radially in an outward direction. The position of the occlusion is changed by the movement of the rollers as they are driven along the tube, thus realizing the pumping of the fluid. An advantage of peristaltic pumps is that they can deliver precise quantities relatively well. Because only the tube comes into contact with the fluid that is conveyed, a peristaltic pump can be cleaned quickly and cost-effectively by replacement of the tube.

Due to the contact between the rollers and the tube, combined with flexing and friction, the tube can be subject to triboelectric charging. Plastic surfaces are most prone to this type of charging. Thus the contact and friction of the surfaces of the stator and the rotor—i.e. the rollers driven by the rotor—with the tube generate and exchange charges, and when the rollers are removed from the tube these charges cannot be equalized with sufficient rapidity, and remain as electrostatic charges on the corresponding surfaces. The charges arise due to the fact that the tube is initially pressed by the pressing force of the rollers against both the occlusion bed, as the corresponding contact surface of the stator, and the rollers. As the rollers move on, each roller lifts off of its section of the tube, with the result that the electrostatic charges described above can be formed on the tube, the occlusion bed and the rollers. Additionally, in the area in which the tube exits the pump, the rollers lift completely off of the tube. When the rotor then turns further, and each roller again comes into contact with the tube in the area in which the tube enters the pump, electrostatic charges which have collected on the roller can be transferred to the tube and thereby cause a corresponding interfering impulse. These charges lead to an electrostatic charging of the tube, and in particular its outer surface. The charge separation is effected according to the triboelectric effect due to the fact that different materials have differing electron affinity, and when such materials are separated the electrons cannot move with sufficient freedom to equalize the charges.

Alongside the generation of charges from the contact between the roller and the tube, electrostatic charges can also be formed between the tube and the occlusion bed. This is because, as the rotor moves on and each roller lifts off of the corresponding section of the tube, the elastic resilience within the tube causes its restitution to its basic cylindrical shape, with the result that the tube is no longer in contact with its occlusion bed over a surface, but only along a line. This is a partial lifting of the tube off of the tube bed, through which electrostatic charges can arise.

In the medical field, diagnosis devices with high-impedance measurement inputs, such as ECG devices, are used, and the measurement results of these devices can be disrupted or distorted by the electrostatic charges on the tube. This problem is known, and the responsible German federal agency BFARM [Federal Institute for Drugs and Medical Devices] recommends that it be alleviated by potential equalization between the devices, i.e. the pump and the diagnosis device, without, however, eliminating the problem. These electrostatic charges appear, as described above, in the form of an electrical interfering impulse, particularly when the rolls are pressed down onto the tube. Dry ambient air can exacerbate this problem. Anti-static sprays are known as an inadequate approach to the elimination of this type of charge. Tubes composed of special materials, e.g. materials containing metal, are also unsuitable for reducing the charges, for reasons of biocompatibility.

Although some ECG devices can filter out these disturbances, and in particular the interfering impulses, by the use of suitable filters, such filters cannot be used in special applications, for example the examination of signals from cardiac pacemakers, because the cardiac pacemaker signals to be measured strongly resemble the interference signals. It is possible, as in U.S. Pat. No. 3,580,983, to attach an electrical grounding cable directly to the tube to prevent charging. Additionally, tube connectors with galvanic contacts for grounding are known from WO 2004/108206 A1. Or, as disclosed in WO 2009/044220 A1, grounding connectors can be attached to the applicable tubes. This prior art has the disadvantage that it addresses less the creation than the transmission and detrimental effects of the charges. The approach to this chosen in U.S. Pat. No. 5,127,907 is that parts that are in motion relative to each other are composed of similar materials. Another disadvantage that is apparent in the known solutions is the additional equipment needed and the additional costs.

The object of the present invention is to prevent or at least reduce disruptive influences of electrostatic charges or electrical impulses from a peristaltic pump upon electrical devices.

SUMMARY OF THE INVENTION

This problem is solved by a peristaltic pump for use in medical technology comprising a stator and a rotor, whereby the stator has an occlusion bed which forms the contact area with a tube accommodated within, and the rotor is provided with rolling elements suitable for occluding a tube accommodated between the occlusion bed and the rolling elements. According to the present invention, at least a part of the occlusion bed has an electrically conductive surface for reducing and/or preventing electrostatic charging of the tube.

According to the invention, a peristaltic pump for use in medical technology is thus provided, with a stator and a rotor, whereby the stator has an occlusion bed which forms the contact area with a tube accommodated within it, and the rotor is provided with rolling elements, which are suitable for occluding a tube accommodated between the occlusion bed and the rolling elements. The occlusion bed thereby has at least in part an electrically conductive surface for reducing and/or preventing electrostatic charging of the tube. The rolling elements can thereby be rollers or spheres and the occlusion bed can also have a plurality of separate areas of the conductive surface. In the area over which a rolling element has rolled, the tube has the tendency, by reason of its internal resilience, to deform back to its original cylindrical shape, and during this deformation areas of the tube lift from the occlusion bed. It has been recognized that electrostatic charges can be generated on the surface of the tube due to a lack of charge exchange in this separation area. The charge exchange is aided by a metallic surface of the occlusion bed, and the generation of electrostatic charges is prevented or at least reduced.

Through this embodiment, no additional devices that are visible to the user are necessary on the peristaltic pump and/or on the tube system in order to prevent the electrostatic charges. The operating personnel are not required to perform any additional setting-up steps, and have an unchanged optical impression of the peristaltic pump and the medical device in which the peristaltic pump may be integrated.

A potential equalization, in particular in the form of a ground connection, can further be provided on the electrically conductive surface. This potential equalization can take place in that sensitive electronic devices which are located near the peristaltic pump and could be disrupted are brought to the same electrical potential as the peristaltic pump and in particular its occlusion bed, for example by means of an electrical conductor. A potential equalization can also be created by a grounding in the electrical supply network which allows charges to be freely equalized and thus prevents or at least effectively reduces the charging of the surface of the tube. An electrical resistance provided preferentially between the potential equalization and the electrically conductive surface limits the leakage current and thus prevents a transmission of interference signals via the ground connection to other devices connected there.

Further, the rolling elements preferentially also have an electrically conductive surface, which in the case of cylindrical rollers is the circumferential surface, and there is an electrically conductive contact from these surfaces to the electrically conductive surface of the occlusion bed. In this manner there is same electrical potential on both sides of the tube which is located between each rolling element and the occlusion bed, with the result that the generation of electrostatic charges on the tube is thereby further reduced.

In a further embodiment of the invention, the entire occlusion bed has a continuously electrically conductive surface. In principle the occlusion bed can have a conductive surface which is only partial, i.e. in certain sections only, but such a continuously conductive surface improves the charge equalization. It is particularly advantageous that the initial generation of electrostatic charges is prevented (or at least reduced) by this means, which is markedly more effective than subsequently dissipating or equalizing charges that may have been generated. This also ensures that no raised and/or uneven areas are produced in the occlusion bed, which could impair the rolling process of the rolling elements and thereby the pumping effect, and could have detrimental effects on the durability of the tube.

The peristaltic pump can be designed as a peristaltic roller pump, i.e. the occlusion bed has a cylindrical surface facing inwards and the rolling elements are realized as rollers. Peristaltic roller pumps can be manufactured cost-effectively, and have good properties with respect to the delivery of accurate quantities. As an alternative to this, the peristaltic pump can also have spherical pressing or rolling elements, as will be described in more detail in a further embodiment below.

Additionally, the cylindrical surface of the occlusion bed can have openings in one or two places, to serve as entry or exit points for the tube in and out of the peristaltic pump. This enables the tube to be accommodated without kinks.

In a further embodiment the stator is manufactured as an injection molded part, and the said electrically conductive surface is the surface of a molded-in metallic insert, or a molded-in metallic foil. The insert molding of a metal part enables a good mechanical bonding of the metal with the plastic. Because the plastic of the injection molded part is composed of an electrically non-conductive plastic, the charges which can develop on the occlusion bed are not transferred via the plastic to other areas of the pump and/or a corresponding medical device. The plastic material of the stators is thereby electrically non-conductive, so that the charges cannot propagate over the stator.

In a further embodiment the insert can have a basic cylindrical shape with a flange which is preferably around its entire circumference and facing radially inwards. This geometry corresponds approximately to that of a can with a base which lends the basic cylindrical shape stiffness preventing deformation. In this it is preferable to provide a concentric opening in the base, through which the drive shaft of the rotor can be passed. Alternatively the flange can face outwards, i.e. when insert is molded in this flange points in the direction of the plastic and ensures a good metal-plastic bond.

In an alternative embodiment the said electrically conductive surface of the occlusion bed can also be realized by a conductive coating of a previously manufactured injection molded part. The occlusion bed must have a high degree of curvature, which is also well obtainable with modern injection molding machines. A coating of an injection molded part that is manufactured in such a way, for example a galvanic coating or lamination, retains the precision of the surface and in particular its curvature. It is also possible to insert an electrically conductive metal part, such as for example a stainless steel panel, in a correspondingly molded receptacle in the peristaltic pump, which is a simpler manufacturing process, and one which is more cost-effective in comparison with an injection molding; the pressure exerted by the rolling elements will give this metal part a good contact with the injection molded cylindrical surface of the occlusion bed.

Further, a medical device can comprise a suitable peristaltic pump, whereby the device has a front panel facing the user with operating and functional elements, which is formed as an injection molded part. In this device, the peristaltic pump with the occlusion bed is integrated as a single piece in the front panel with operating and functional elements. This creates a uniform front of the device and hence an attractive overall design.

BRIEF DESCRIPTION OF THE DRAWINGS

The invention is elucidated in detail with the aid of the drawing. The drawing shows.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
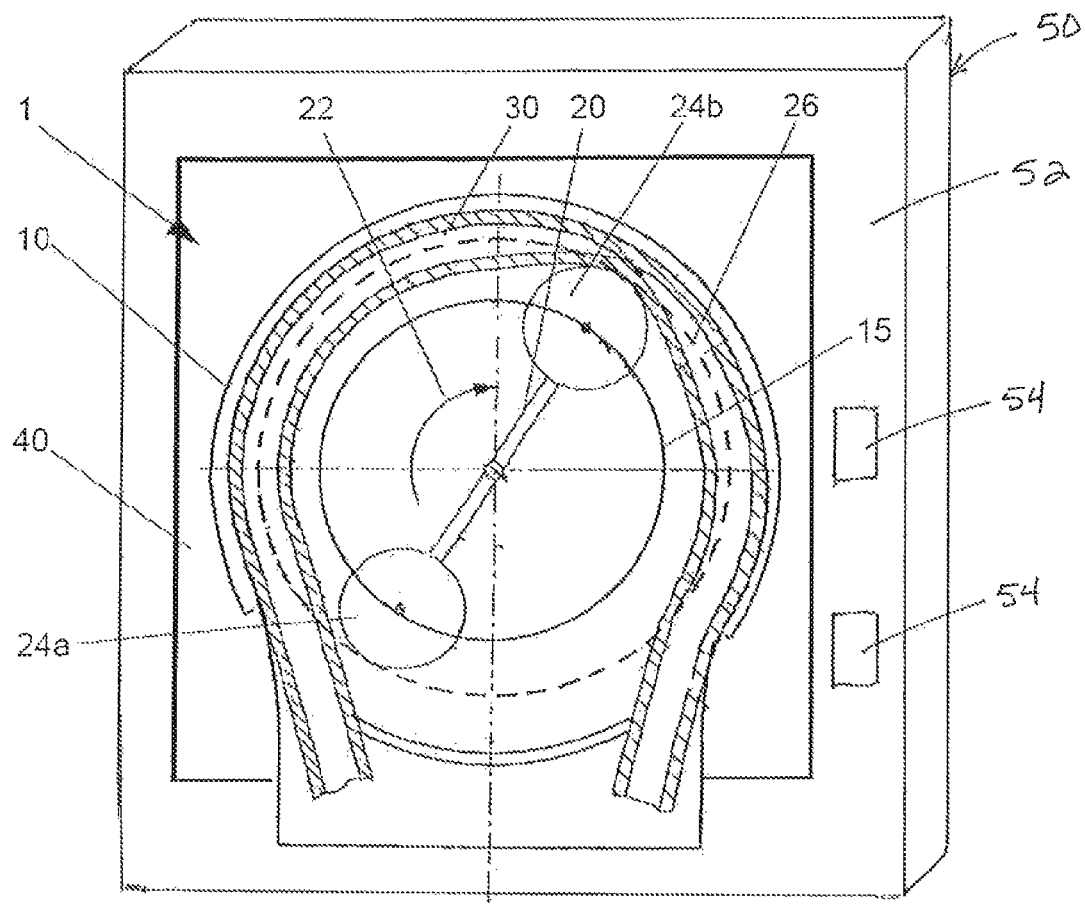
FIG. 1 a schematic diagram of a peristaltic roller pump,
FIG. 2 a plan view of a corresponding peristaltic roller pump,
FIG. 3 a variant of an insert and
FIG. 4 a further variant of the insert.

FIG. 1 shows a schematic diagram of a peristaltic roller pump. In this a tube 30 is disposed in a cylindrical receptacle of an insert 10 and is thereby in contact with the inner side of the insert over approximately 270° of its circumference. This surface will be designated hereinafter as the occlusion bed 12. A rotor 20 having two drive arms is disposed coaxially to the insert 10, with a rolling element 24a, 24b in the form of a cylindrical roller rotatably mounted on each drive arm. The rotor is driven in the direction of drive 22 via a motor (not shown). The upper rolling element 24b thereby presses radially outwards against the tube 30 in such a manner that the tube is locally occluded. When the drive now moves the rotor onwards, this occluded point moves in a clockwise direction. The lower rolling element 24a thereby comes into contact with the tube, and occludes the tube in an equivalent manner, thus conveying the volume of fluid between the two closed points in the longitudinal direction of the tube. The tube is thereby in a fixed position relative to the insert 10 and its occlusion bed 12, and a rolling motion takes place between the rolling elements 24a, 24b and the tube. The outer rolling radius 26 of the rolling elements is thereby so dimensioned as to be essentially smaller than the inner radius of the insert 10 by twice the thickness of the wall of the tube 30, in order thus to close the tube adequately without squeezing it too much.

Figure 2:
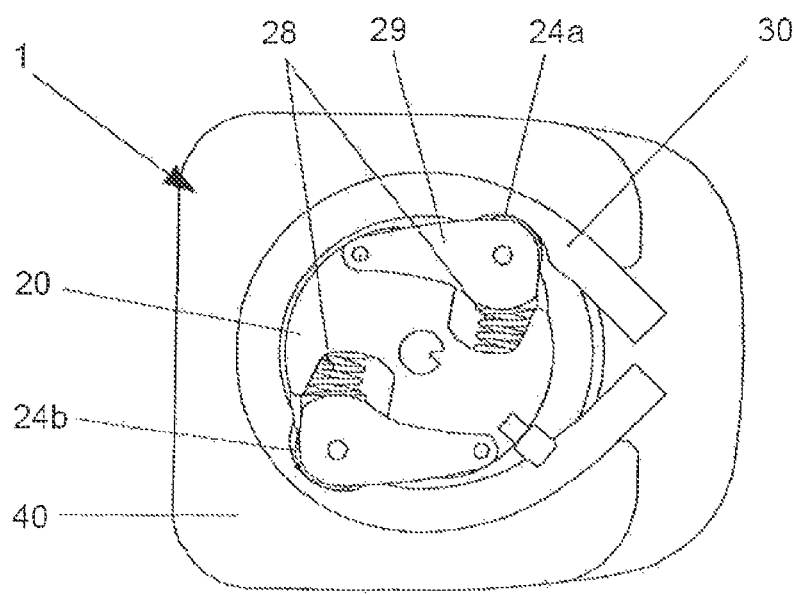

In order to realize a desired radial pressing force exerted by the rolling elements 24a, 24b against the tube 30, each rolling element can, as shown in FIG. 2, be provided with a compression spring 28 which is attached to the rotor 20, and by means of a roller arm 29 presses the rollers 24a, 24b outwards. Each of the two roller arms 29 is mounted in a swiveling manner on the rotor 20, has a surface on which the compression spring 28 can press, and has a mounting for one of the rollers 24a, 24b. A greater number of rolling elements can also be used.

Figure 3:
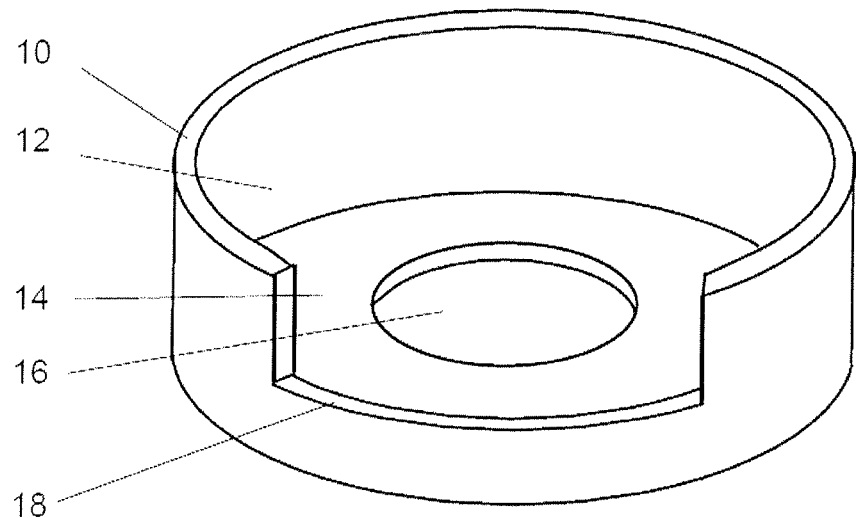

The insert 10 is thereby implemented as a type of can, composed of a metallic material such as for example stainless steel plate. This means that it has a basic cylindrical shape and is bounded at one axial end by a flange 14 which extends radially inwards and leaves a coaxial opening 16 free for the drive shaft of the rotor 20. The cylindrical front face of the flange 14 is shown in FIG. 1 and FIG. 3, with the inner diameter of the flange end 15. According to FIG. 1, the tube is guided into the inner part of the insert 10 through an opening 18 which is provided in the basic cylindrical shape of the insert 10 at a distance from the flange. Because the opening runs for a full 90°. of the circumference, rolling takes place over barely 270°. of the occlusion bed. In order for the peristaltic pump to convey fluid, at least one roller element must occlude the tube at all times, and thus if two roller elements are used it would be sufficient if rolling took place over 180°.

As an alternative to the embodiment in FIG. 3, the flange 14 can also point radially outwards, or an outward facing flange can be provided on the other end of the insert in addition to the flange 14 shown in FIG. 3.

In the preliminary remarks the technical effect was described by which, in conventional peristaltic pumps, triboelectric charges and interfering impulses are generated when the rollers travel along the tube, the tube lifts from its occlusion bed, and above all when each roller is pressed down onto the tube in the area in which the tube enters the pump. Such charges and interfering impulses are generated particularly when plastic surfaces come into contact with each other.

In the present invention the insert 10 is composed of a metallic material, and thus the occlusion bed, i.e. the cylindrical inner surface of the insert, has an electrically conductive surface. By this means the effect of the charge separation and the corresponding charging is prevented or greatly reduced, since the formation of a local charge preponderance or charge deficit is prevented by the free charge exchange on the conductive surface. Additionally, the rolling elements can also have an electrically conductive surface, and the corresponding electrical charging is thereby also reduced and/or prevented at the point of contact between tube and rolling element.

An electrically conductive connection can also be provided from the rotor 20 with its rollers 24a, 24b to the occlusion bed, for example by means of a sliding contact on the drive shaft of rotor 20 which is connected in an electrically conductive manner (not shown) with the insert 10, and thus the effect of preventing charging is further reinforced.

In the embodiment described here, the entire occlusion bed is configured to be electrically conductive. However, a significant reduction in the interfering impulses can be achieved purely by providing the occlusion bed with conductive and grounded sections only in the area in which the tube 30 enters and exits. Charges which are located on the outside of the tube, or corresponding interfering impulses, can be dissipated by the grounding.

The insert 10 can be manufactured cost-effectively, with a precise curvature and with a smooth surface, from sheet metal by a deep drawing process. This insert is placed in an injection mold. In the injection mold the insert is molded in and forms a positive and fixed connection with the injection molded body of the peristaltic pump. The peristaltic pump can also be integrated in the front panel of the corresponding medical device, in order to be easily accessible to the user. In this case the insert is injection molded into the corresponding front panel.

Alternatively, the insert can also be composed of a metal foil, which can be placed in the injection mold in annular form and molded in.

Alternatively, the metallic surface of the occlusion bed can also be subsequently applied to a plastic injection molded part. The MID (Molded Interconnection Device) technology can be used for this type of conductive coating. This technology is primarily used for the creation of three-dimensional conductive paths for electrical circuits, but it is also possible to create continuously conductive surfaces in this manner. To do this a suitably coatable plastic is used, which is coated galvanically with an appropriate metal layer. If this coatable plastic is used in a two component injection molding process exclusively in the area of the occlusion bed, another material can be used for the front of the device. A stainless steel foil or stainless steel panel can also be clamped and/or glued into the cylindrical receptacle.

The insert 10 (see FIG. 3) has an opening 18, which serves according to FIG. 1 as both the entry and the exit for the tube, so that the rolling length, i.e. the surface of the occlusion bed over which the tube is pressed, is 270π. As an alternative, an insert according to FIG. 4 can be used, which has two smaller openings opposite each other. This insert can be used in a peristaltic pump in which the tube is led into the cylindrical area on one side, guided through one and a half revolutions inside, and leaves the pump on the opposite side. The tube can also be guided through more revolutions inside the pump.

Figure 4:
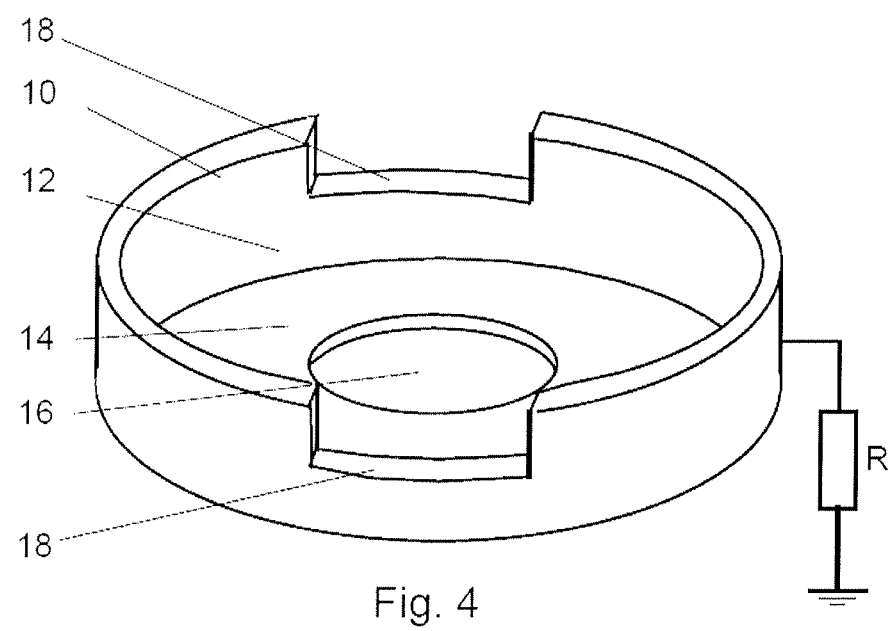

FIG. 4 shows schematically a resistance R which is electrically connected between the insert 10 and a potential equalization or in particular a ground connection. This potential equalization can also be connected with the rotor 20. The resistance R has the effect of limiting the leakage current of the interference signal. In this manner, when a sensitive device is connected to the potential equalization or the ground connection, the transmission of interference signals via the potential equalization to this device is prevented.

Further, the peristaltic pump 1 may be part of a medical device, generally designated by reference numeral 50, as shown in FIG. 1. Such a medical device may be a dialysis, infusion and/or transfusion apparatus. The device 50 has a front panel 52 facing the user with operating and functional elements 54, which is formed as an injection molded part. In this device, the peristaltic pump 1 with the occlusion bed 12 is integrated as a single piece in the front panel 52 with operating and functional elements 54. This creates a uniform front of the device and hence an attractive overall design.

So far in the example embodiment a peristaltic roller pump has been described, which uses rollers as the rolling or pressing elements. The invention can be equally applied to peristaltic pumps with spherical rolling elements. Such a peristaltic pump resembles a radial ball bearing, in which the outer race is the stator, which has a concave circumferential recess in which the tube lies and is preferably occluded locally by two successive outward pressing spheres. The driving of the pump is transmitted directly onto the spheres, which are guided within a cage in a manner similar to a radial ball bearing.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A peristaltic roller pump for use in medical technology comprising: a stator and a rotor, said stator being injection molded from an electrically non-conductive plastic and having an occlusion bed with a cylindrical surface facing inwards which forms the contact area with a tube accommodated within, and the rotor being provided with rollers for occluding the tube accommodated between the cylindrical surface of the occlusion bed and the rollers, at least a part of the inward facing cylindrical surface of the occlusion bed having an electrically conductive surface for at least one of reducing and preventing electrostatic charging of the tube during pump operation, said electrically conductive surface being the surface of one of a molded-in metallic insert and a molded-in metallic foil insert, said insert having a basic cylindrical shape with a flange, said flange facing radially inwards and being disposed around an entire circumference of said insert.

2. The peristaltic roller pump according to claim 1, wherein the electrically conductive surface has a potential equalization.

3. The peristaltic roller pump according to claim 2, wherein the potential equalization is in the form of a ground connection.

4. The peristaltic roller pump according to claim 2, wherein an electrical resistance (R) is provided between the potential equalization and the electrically conductive surface.

5. The peristaltic roller pump according to claim 1, wherein the rollers have an electrically conductive surface and an electrically conductive contact exists from said roller surfaces to the electrically conductive surface of the occlusion bed.

6. The peristaltic roller pump according to claim 1, wherein the entire occlusion bed has a continuously electrically conductive surface.

7. The peristaltic roller pump according to claim 1, wherein the contour of the occlusion bed has openings in one or two places, to serve as entry or exit for the tube from the peristaltic pump.

8. The peristaltic roller pump according to claim 1, wherein the electrically conductive surface was produced by a local conductive coating of an injection molded part.

9. A medical device for extracorporeal blood treatment comprising a peristaltic roller pump having a stator and a rotor, said stator being injection molded from an electrically non-conductive plastic and having an occlusion bed with a cylindrical surface facing inwards which forms the contact area with a tube accommodated within, and the rotor being provided with rollers for occluding the tube accommodated between the occlusion bed and the rollers, at least a part of the inward facing cylindrical surface of the occlusion bed having an electrically conductive surface for at least one of reducing and preventing electrostatic charging of the tube during pump operation, the electrically conductive surface being the surface of one of a molded-in metallic insert and a molded-in metallic foil insert, said insert having a basic cylindrical shape with a flange, said flange facing radially inwards and being disposed around an entire circumference of said insert.

10. The medical device according to claim 9, wherein the peristaltic roller pump with the occlusion bed is integrated as a single piece in an injection molded front panel of the medical device that has operating and functional elements.

11. The medical device according to claim 9, wherein the medical device is one of a dialysis apparatus, an infusion apparatus and a transfusion apparatus.

* * * * *